United States Patent
Frappier et al.

(10) Patent No.: US 7,943,633 B2
(45) Date of Patent: May 17, 2011

(54) ALKALOID COMPOUNDS AND THEIR USE AS ANTI-MALARIAL DRUGS

(75) Inventors: François Frappier, Paris (FR); Marie-Pierre Frappier, legal representative, Paris (FR); Jérôme Frappier, legal representative, Paris (FR); Dominique Mazier, Paris (FR); Maëlle Carraz, Polssy (FR); Jean-François Franetich, Gagny (FR); Akino Jossang, Paris (FR); Roger Joyeau, Paris (FR); Phillippe Rasoanaivo, Antananarivo (MG)

(73) Assignees: Universite Pierre et Marie Curie (Paris VI), Paris (FR); Centre National de la Recherche Scientifique, Paris (FR); Museum National d'Histoire Naturelle, Paris (FR); Institut Malgache de Recherche Appliquee, Antananarivo (MG)

(*) Notice: Subject to any disclaimer, the term of this patent is extended or adjusted under 35 U.S.C. 154(b) by 979 days.

(21) Appl. No.: 11/583,729

(22) Filed: Oct. 20, 2006

(65) Prior Publication Data

US 2008/0038390 A1 Feb. 14, 2008

Related U.S. Application Data

(63) Continuation of application No. PCT/EP2005/005239, filed on Apr. 21, 2005.

(30) Foreign Application Priority Data

Apr. 22, 2004 (EP) .................................. 04291055

(51) Int. Cl.
*A61K 31/4748* (2006.01)
*C07D 221/28* (2006.01)

(52) U.S. Cl. .......................................... 514/289; 546/74
(58) Field of Classification Search .................. 514/289; 546/74

See application file for complete search history.

(56) References Cited

FOREIGN PATENT DOCUMENTS

WO WO 00/14070 3/2000
WO WO 00/50404 8/2000

OTHER PUBLICATIONS

Kashiwaba, N. et al.: Alkaloidal constituents of the leaves of *Stephania cepharantha* cultivated in Japan: structure of Cephasugine, a new morphinane alkaloid. Chem. Pharm. Bull., vol. 45, pp. 545-548, 1997.*
Ogino, T. et al.: New alkaloids from the root of *Stephania tetrandra* ( Fen-Fang-Ji ). Heterocycles, vol. 48, pp. 311-317, 1998.*
Patent Abstracts of Japan vol. 0121, No. 86 (C-500), May 31, 1988 & JP 62 289565 A (Toubishi Yakuhin Kogyo KK), Dec. 16, 1987 cited in the application, abstract.
Patent Abstracts of Japan vol. 0121, No. 48 (C-493), May 7, 1988 & JP 62 263158 A (Toubishi Yakuhin Kogyo KK), Nov. 16, 1987 cited in the application, abstract.
Waters N.C. et al; Expert Opin. Ther. Patents, vol. 14, No. 8, 2004, pp. 1125-1138, XP002295586 the whole document.

* cited by examiner

Primary Examiner — Charanjit S Aulakh
(74) Attorney, Agent, or Firm — Young & Thompson

(57) ABSTRACT

Anti-malarial alkyloid compounds have the formula:

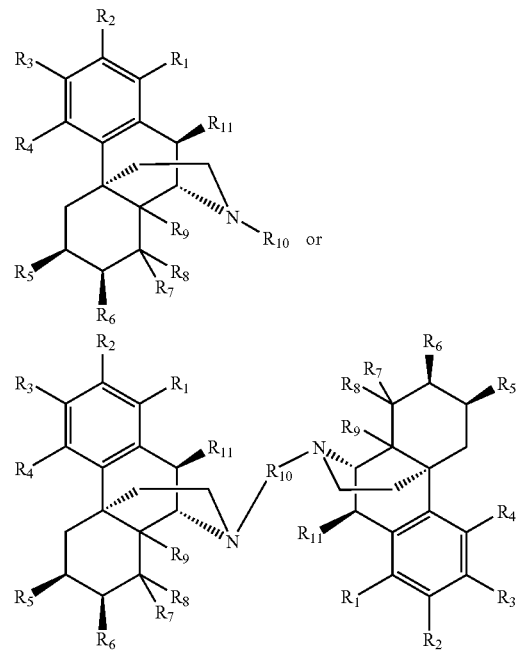

wherein $R_1$-$R_{11}$ have various disclosed values or their pharmaceutically acceptable salts, and pharmaceutical compositions containing the same.

7 Claims, 1 Drawing Sheet

ALKALOID COMPOUNDS AND THEIR USE AS ANTI-MALARIAL DRUGS

The present invention concerns alkaloid compounds and their use as a medicament. These compounds and derivatives are particularly useful against malaria in a prophylactic and/or curative treatment. Therefore, the present invention also concerns pharmaceutical compositions comprising the new compounds and the use of the compounds in a process for the preparation of anti-malarial compositions. Furthermore in another aspect of the invention, it concerns a process of preparation of these compounds.

Malaria is a serious health care problem posing a great menace to society due to the number of patients infected and the mortality rate of patients, as evidenced by about 300 million patients attacked annually predominantly in tropical and subtropical regions, causing about 2 million deaths in these areas.

Malaria is usually treated by administering chloroquine, pyrimethamine, quinine, proguanil, primaquine, artemisinin compounds, etc. . . . , even combinations thereof, but effective treatments have become difficult with these conventional anti-malarial drugs because most of the malarial parasites eventually become resistant to these anti-malarial drugs. Most of the usual anti-malarial compounds are known to be active at the blood stage of the parasites but not at the hepatic stage.

Some of the known chemical compounds to treat malaria are not free of side effects, this rendering their long-term use deleterious in some aspects and limiting the use of these compounds.

There is therefore still a need for compounds having an efficiency against malaria, without their usual drawbacks, and not only at the blood stage but also at the hepatic stage, this conferring to the compounds a prophylactic effect. Furthermore, there is a need for anti-malarial drugs which are easy to formulate in pharmaceutical compositions.

The applicants have now found that some compounds isolated from *Strychnopsis thouarsii* and also synthetic derivatives thereof have good anti-malarial activity, particularly on the hepatic stage (also call exoerythrocytic stage) of *Plasmodium*, contrary to most of conventional antimalarial drugs which are only active on the erythrocytic cycle.

JP 62-263158 describes sinoccoculine as an anti-tumoral active agent and JP 62-289 565 describes tetracyclic alkaloids and their anti-tumoral activity, the compounds being extracted from *Cocculus sarmentosus* or *Cocculus trilobus*.

The present invention thus concerns the use of the compounds of formula I or II below and their derivatives as medicaments, particularly as anti-malarial compounds.

Amongst them, most are new. In another aspect, the invention concerns chemical compounds having the formula

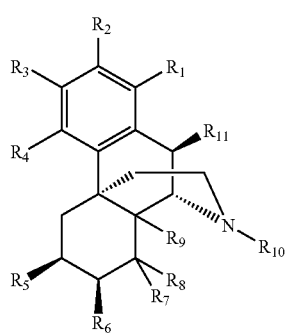

(I)

wherein
$R_1$ is H or $OC_iH_{2i+1}$ with i between 0 and 6;
$R_2$ is H or $OC_jH_{2j+1}$ with j between 0 and 6;
$R_3$ is H or $OC_kH_{2k+1}$ with k between 0 and 6;
$R_4$ is H or OH;
$R_5$ is OH or $OC_mH_{2m+1}$ with m between 1 and 6 or an acetoxy group or an oxo group;
$R_6$ is OH or $OC_nH_{2n+1}$ with n between 1 and 6 or an acetoxy group or an oxo group;
$R_7$ is $OC_pH_{2p+1}$ with p between 0 and 6;
$R_8$ and $R_9$ may be similar or different and represent H or $OC_qH_{2q+1}$ with q between 0 and 6, or Hal where Hal is Cl, Br, F or I, or form together a covalent bond whereby the bond is a double bond or form with an oxygen atom an ether bond (epoxy group);
$R_{10}$ is H or $C_rH_{2r+1}$ with r between 1 and 12 or an unsaturated alkyl group or a cycloalkyl group (tri- to hexa-) unsaturated or not, with or without heteroatoms; or an aromatic or a polycyclic aromatic group with or without heteroatoms; or $C_sH_{2s}$-A with s between 1 and 12 and whereby A is a saturated or (tri- to hexa-) unsaturated cycloalkyl group, with or without heteroatoms or an aromatic or a polycyclic aromatic group with or without heteroatoms or A is $C_6H_{5-t}$-$(Hal)_t$ with t between 1 to 5 or $C_6H_{5-u}$—(O—$C_vH_{2v+1})_u$ with u between 1 to 5 and v between 0 and 6; or $R_{10}$ represents two substituents similar or different rendering the nitrogen atom quaternized, or an oxygen atom (nitrone group) and in which case the bond between the nitrogen atom and $C_9$ is a double bond; or $R_{10}$ represents $CH_2CH_2[OCH_2CH_2]_w$ $OCH_2CH_2$—B with w between 0 and 10 and where B is OH, O-D or NH-D where D is a $C_1$-$C_{12}$ alkyl group bearing an electrophilic function such as an isothiocyanate;
$R_{11}$ is H or OH or $OC_xH_{2x+1}$ with x between 1 and 6 or Hal where Hal is Cl, Br, F or I; or an acetoxy group or a sulfonate ester group or an oxo group;
or $R_{10}$ and $R_{11}$ may represent an isoalkylidene group;

or

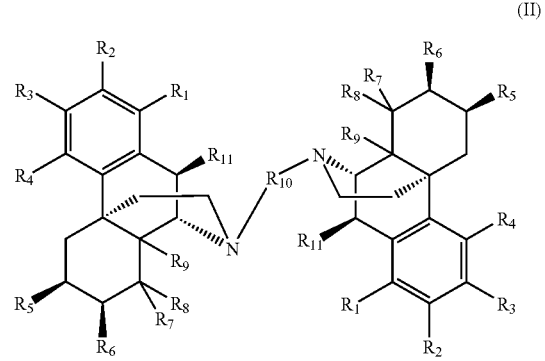

(II)

wherein $R_1$, $R_2$, $R_3$, $R_5$, $R_6$, $R_7$, $R_8$ and $R_9$ are defined as above,
$R_4$ is H or OH or $OC_lH_{2l+1}$ with l between 2 and 6;
$R_{10}$ is $C_yH_{2y}$ with y between 1 and 12 or $CH_2CH_2$ $[OCH_2CH_2]_zOCH_2CH_2$ with z between 0 and 10; and
$R_{11}$ is H or OH or $OC_xH_{2x+1}$ with x between 1 and 6 or Hal where Hal is Cl, Br, F or I; or an acetoxy group or a sulfonate ester group or an oxo group;
and all stereoisomers and optical isomers thereof,
with the proviso that in formula (I) (1) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bound and $R_1$ is H; and (2) $R_1$ is not H when $R_2$ is H and $R_3$ and $R_7$ are $OCH_3$, $R_4$, $R_5$ and $R_6$ are OH and $R_8$ and $R_9$ represent a double bound and $R_{10}$ is H, and particularly with the proviso that in formula (I) (1) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bound and $R_1$, $R_{10}$ and $R_{11}$ are H; and (2) $R_1$ is not H when $R_2$ is H and $R_3$ and $R_7$ are $OCH_3$, $R_4$, $R_5$ and $R_6$ are OH and $R_8$ and $R_9$ represent a double bound and $R_{10}$ and $R_{11}$ are H, which are known from JP 62-263158 and JP 62-289565.

In the following, the proviso is defined in that, in the compounds of formula I, (1) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bound and $R_1$ is H; and (2) $R_1$ is not H when $R_2$ is H and $R_3$ and $R_7$ are $OCH_3$, $R_4$, $R_5$ and $R_6$ are OH and $R_8$ and $R_9$ represent a double bound and $R_{10}$ is H, but also in that in formula (I) (1) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bound and $R_1$, $R_{10}$ and $R_{11}$ are H; and (2) $R_1$ is not H when $R_2$ is H and $R_3$ and $R_7$ are $OCH_3$, $R_4$, $R_5$ and $R_6$ are OH and $R_8$ and $R_9$ represent a double bound and $R_{10}$ and $R_{11}$ are H.

Particularly, the invention concerns the compounds of formula I with the above proviso and the use of compounds of formula I without the proviso for their antimalarial activity. Amongst them, the preferred compounds are those wherein $R_8$ and $R_9$ form a double bound, and $R_1$ and $R_2$ are H, and particularly the compounds wherein $R_{11}$ is OH.

According to an aspect of the invention, $R_{10}$ can represent H or $C_rH_{2r}$-A with r between 1 and 12 and whereby A is H or a cycle $C_sH_{2s-1}$ with s between 3 and 6 or an aromatic cycle or an aromatic polycycle or an aromatic cycle substituted as $C_6H_{5-t}$-(Hal)$_t$ with t between 1 to 5 and where Hal is Cl, Br, F or I, or as $C_6H_{5-u}$—(O—$C_vH_{2v+1}$)$_u$ with u between 1 to 5 and v between 0 to 6, or as $C_6H_{5-w}$—(NH$_2$)$_w$ with w between 1 to 2; or $R_{10}$ represents two substituents similar or different rendering the nitrogen atom quaternized, or an oxygen atom; or $R_{10}$ represents $CH_2$—$CH_2$—[O—$CH_2$—$CH_2$]$_x$O—$CH_2$—$CH_2$—B with x between 0 and 10 and whereby B is H or OH or $NH_2$ or N=C=S.

The preferred compounds are described hereafter namely in the examples and the detailed description.

More particularly, the invention thus concerns 4,6,7,10-tetrahydroxy-8,14-didehydro-3,8-dimethoxymorphinan and its derivative N-methyl-, N-propyl-, N-4-methoxybenzyl-, N4-hydroxybenzyl-, N-4-bromobenzyl- or N-cyclopentyl-4,6,7,10-tetrahydroxy-8,14-didehydro-3,8-dimethoxy-morphinan, as well as their pharmaceutically acceptable salts, and their optical isomers including racemates, and more particularly the isomers having the optical configuration (6S, 7S, 9R, 10R, 13S).

More particularly, the invention concerns (1)

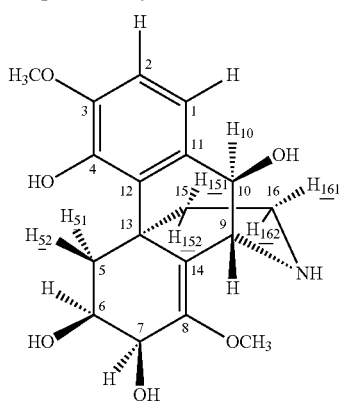

and the use of (2)

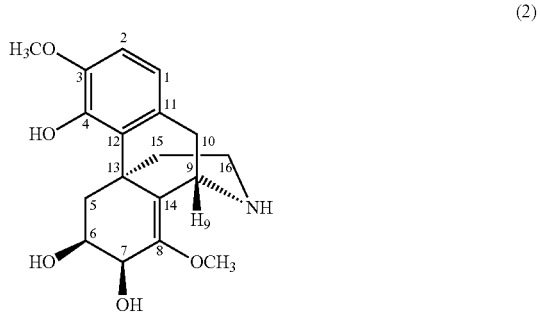

as anti-malarial compounds.

Furthermore, the invention concerns pharmaceutical compositions containing the compounds of formula I or II as above defined and stereoisomers and optical isomers and pharmaceutically acceptable salts thereof as an active agent together with an pharmaceutically acceptable vehicle, particularly an aqueous vehicle.

It also concerns pharmaceutical compositions comprising a compound of formula I or formula II as above defined, without the proviso together with at least one second antimalarial compound and a pharmaceutically acceptable vehicle.

It also concerns the use of these compounds for the preparation of a pharmaceutical composition useful in the treatment of malaria, said composition comprises at least a compound of formula I or II without the proviso and another anti-malarial compound.

The invention further concerns the use of the compounds of formula I or II without the proviso and all the stereoisomers and optical isomers thereof, for the preparation of a pharmaceutical composition useful in the prophylactic or curative treatment of malaria.

According to a further aspect, the invention concerns pharmaceutical compositions comprising an isolated extract of *Strychnopsis thouarsii* having an anti-malarial activity.

It also concerns pharmaceutical compositions comprising an isolated extract of *Strychnopsis thouarsii* and at least a compound of formula I or II and a pharmaceutically acceptable vehicle.

The invention also concerns the use of an isolated extract of *Strychnopsis thouarsii* in the preparation of a pharmaceutical composition comprising at least said extract of *Strychnopsis thouarsii* and a pharmaceutically acceptable vehicle, the composition being useful in a prophylactic or curative treatment of the malaria.

The compounds of the invention have an anti-malaria activity particularly drawn to the hepatic stage, which corresponds to the passage of the parasite into the liver and to the infection of the hepatic cells in which the parasites develop to form the hepatic schizonts which, when they are mature (for example in the case of *P. falciparum* on the 6$^{th}$ day after penetration of the sporozoites) release hepatic merozoites by bursting. The third stage is characterized by the infection of the blood erythrocytes by the asexual forms (merozoites) of the parasite; this erythrocytic stage of development corresponds to the pathogenic phase of the disease. The fourth stage corresponds to the formation of the forms with sexual potential (or gametocytes) which will become extracellular sexual forms or gametes in the mosquito. The second stage is also called the exoerythrocytic stage of *Plasmodium*.

The only known and practically used molecules that are active against the hepatic stage are primaquine and atovaquone.

Their use is however limited due to the very toxic nature of primaquine, and due to the rapid development of resistance for atovaquone which is therefore only used in combination with other anti-malarial drugs.

The compounds of the invention are particularly useful for prophylactic and curative treatment of the hepatic stage of malaria. Furthermore, the compounds of the present invention are shown to kill parasites just after transmission by the infected mosquitoes and before it becomes pathogenic by multiplication in the red blood cells. The invention compounds are therefore especially useful for antimalarial prophylaxis particularly as compared with the usual treatments.

Decoction and methanolic extract of the plant were evaluated for their in vitro antimalarial activity through inhibition of *Plasmodium* growth in murine and human hepatocytes, according to tests as described below.

A bioassay-guided fractionation of the plant extract, linking this in vitro test to chromatographic separation techniques was carried out and led to the isolation of active compounds, as described below.

The invention therefore also encompasses isolated extracts of bark or leaves of the plants described therein for use in a pharmaceutical compositions.

The pharmaceutical compositions of the present invention contain a pharmaceutically acceptable carrier in addition to the invention compound(s). The pharmaceutically acceptable carrier depends on the dosage form.

One of the advantages of the invention compounds is their bio-availability. Their solubility in water and aqueous vehicles is a major advantage.

Amongst the pharmaceutically acceptable vehicle, aqueous vehicle are preferred.

When the pharmaceutical compositions are used for oral administration, they may appropriately contain pharmaceutically acceptable carriers including binders such as dicalcium phosphate; disintegrants such as sucrose; dyes; and perfumes such as orange flavor; and solvents such as water, ethanol and glycerol.

When pharmaceutical compositions of the present invention are injectable compositions, suitable pharmaceutically acceptable carriers include sterilized water, isotonic saline and pH buffers. Alternatively, injectable compositions of the present invention may be sterilized powder compositions or lyophilized powder compositions that can be used by simple dissolution in sterilized water. Injectable pharmaceutical compositions of the present invention may contain sugars (glucose, mannitol and dextran, etc.), polyhydric alcohols (glycerol, etc.), and inorganic salts (sodium salts and magnesium salts, etc.).

When pharmaceutical compositions of the present invention are administered by intravenous injection or infusion, they may contain nutrients such as glucose, vitamins, amino acids and lipids.

Pharmaceutical carriers to be added to dosage forms for other administration modes such as nasal administration, inhalation and transdermal administration are also well-known to those skilled in the art.

When pharmaceutical compositions of the present invention are orally administered, they may be in the form of controlled- or sustained-release formulations. Well-known sustained-release formulations include ordinary sustained- or controlled-release formulations such as gel-coated formulations and multicoated formulations as well as site-specific delivery formulations (e.g., burst release at pyloric regions or effervescent delivery to the duodenum). Oral compositions include, for example, tablets, pills, capsules, ampoules, sachet, elixir, suspensions, syrups, etc.

The dosage forms and pharmaceutical carriers mentioned above are described in Remington's Pharmaceutical Sciences, $16^{th}$ ed. (1980), Mack Publishing Company, which is incorporated herein by reference.

Pharmaceutical compositions or unit dose systems of the present invention can be administered via various other routes such as transmucosal (sublingual, nasal, buccal), enteral, dermal administration, suppositories or intravenous infusion. These administration modes depend on the amount of the active compound to be administered, the condition of the patient and other factors.

Among these administration modes, oral administration is especially preferred as well as any mode where the use of aqueous vehicle is of interest.

According to the invention the inventive compound is present in an amount of between 0.001 and 50% by weight of the pharmaceutical composition.

When present in combination with a second anti-malarial compound or as an enhancer of the anti-malarial activity of another anti-malarial compound, the inventive compound is present in an amount between 0.0001 and 20% by weight of the pharmaceutical composition.

In the present invention, the effective amount of inventive compound used for the treatment of malaria is normally 1-1,000 mg/kg weight daily, preferably 5-500 mg/kg weight daily depending on the age, body weight and condition of the patient and the administration mode.

Apart from their obtention by the extraction process, the compounds of the invention can be obtained by synthesis. As it appears from the following examples, the derivatives of (1) and (2) can be prepared according to usual chemical procedures. Particularly alkylation procedures are carried out on products (1) and (2) under suitable alkylation conditions with the corresponding suitable alkylating agents. For example suitable alkylating agents are the corresponding aldehydes or dialdehydes. Suitable conditions can be reductive alkylation conditions.

Furthermore, oxidation and subsequent alkylation can be carried out by usual procedures, and protection of the substituants previously performed, if necessary.

In the following examples, stem bark has been treated to extract the compounds from the plant. However, other parts of the plant might be treated, as well as other species able to produce similar extracts. The leaves of *Strychopsis thouarsii* can also be used, as well as other plants and species. The person skilled in the art can adapt the separation process to the species or part of the plant to be treated.

PREPARATION EXAMPLES

Example 1

Figure 1:
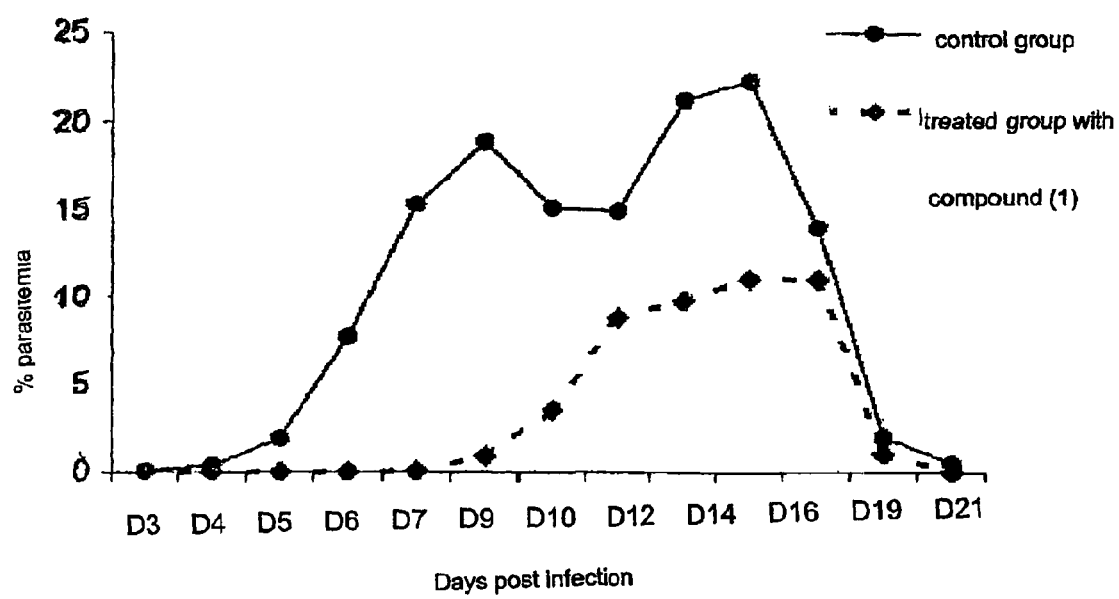
FIG. 1 is a graph indicating the percentage parasitemia days post-infection. The control group is indicated by an •, while the treated group with compound (1) is indicated with ◇.

Extraction Process 500 g powdered *Strychnopsis thouarsii* stem bark was soaked under stirring in MeOH at room temperature for six days, according to the following procedure.

Each 24 hours, the solute was filtrated and the solid residue was treated with 2 l MeOH. The resulting six solutes were pooled and evaporated to dryness under reduced pressure, providing 22 g of methanolic extract.

This extract was dissolved in 2 l H$_2$O and centrifugated at 10,000 rpm for 1 hour. A residue of 10 g was removed, while the supernatant was partitioned three times between H$_2$O and CH$_2$Cl$_2$ (500 mL).

The resulting aqueous extract of 11.7 g was chromatographed on a reversed phase silica gel column (RP-2), eluted with a discontinuous gradient of H$_2$O-MeOH in the proportion of (100-0, 90-10, 80-20, 0-100).

The fractions were pooled according to their TLC profiles into 3 fractions F1 to F3.

The fraction F1 (9.4 g) was further separated on a silica gel column, eluted with CH$_2$Cl$_2$-MeOH—NH$_4$OH (85-15-0.5) leading to 10 fractions F1-1 to F1-10.

The fraction F1-6 was determined to be the most active amongst the obtained fraction, by an evaluation of the biological activity carried out according to the method as described below.

Example 2

Isolation of Compounds (1) and (2)

Compound (1)=4,6,7,10-tetrahydroxy-8,14-didehydro-3,8-dimethoxy-morphinan C$_{18}$H$_{23}$NO$_6$ Compound (2)=4,6,7-trihydroxy-8,14-didehydro-3,8-dimethoxy-morphinan (Sinococuline or FK1000) [CAS Registry Number: 109351-36-2] C$_{18}$H$_{23}$NO$_5$ An aliquot of fraction F1-6 (0.850 g) was chromatographed on a sephadex gel column (LH-20) eluted with MeOH, leading to 4 fractions, F1-6-1 to F1-6-4.

The fraction F1-6-3 (0.368 g) was purified on a silica gel column eluted with CH$_2$Cl$_2$-MeOH—NH$_4$OH (87-13-1), leading to 6 fractions, F1-6-3-1 to F1-6-3-6.

The fraction F1-6-3-4 (0.122 g) was shown to be a mixture of the two compounds (1) and (2).

An aliquot of F1-6-3-4 (0.045 g) was further submitted to a preparative silica gel TLC migrating in CHCl$_3$—NH(C$_2$H$_5$)$_2$ (70-30), leading to 2 fractions, F1-6-3-4-1 (0.01 g) and F1-6-3-4-2 (0.028 g).

The first fraction was submitted to a silica gel column filtration with CH$_2$Cl$_2$-MeOH—NH$_4$OH (70-30-3), providing pure compound (2) (0.004 g), while the second fraction, under the same conditions, afforded pure compound (1) (0.019 g).

Example 3

Isolation of Compounds (1) and (2)

An aliquot of fraction F1-6 (0.22 g) was straightly subjected to a preparative silica gel TLC migrating in CHCl$_3$-MeOH—NH$_4$OH (75-25-3.5), providing compound (1) (0.04 g), while bands corresponding to less polar products were pooled and submitted to a second preparative TLC migrating in CHCl$_3$-MeOH—CH$_3$COOH—H$_2$O (75-18-4-3), leading to 3 fractions, F1-6-1' to F1-6-3'.

The fraction F1-6-1' (0.012 g) was subjected to a silica gel column filtration with CH$_2$Cl$_2$-MeOH—NH$_4$OH (90-10-1), providing pure compound (2) (0.004 g).

Example 4

Analytical Data of Compounds (1) and (2)

1) Compound (1)

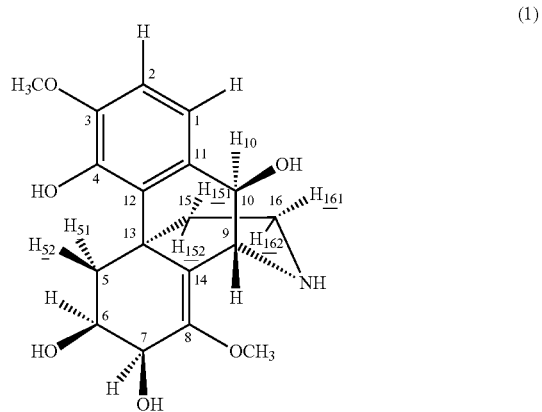

(1)

a) NMR data of (1) in CD$_3$OD and its attribution by 2D NMR (400 MHz):

| Carbon number | δ H (multiplicity, J in Hz) | δ C |
| --- | --- | --- |
| 1 | 6.86 (d, 8.4) | 121.93 |
| 2 | 6.90 (d, 8.4) | 110.67 |
| 3 | — | 149.18 |
| 4 | — | 145.07 |
| 5$_1$ | 2.95 (dd, 3.3, 13.4) | 36.51 |
| 5$_2$ | 2.19 (dd, 13.4, 13.4) | |
| 6 | 3.86 (m, 2.7, 3.3, 13.4) | 68.60 |
| 7 | 4.28 (d, 2.7) | 66.91 |
| 8 | — | 148.49 |
| 9 | 4.33 (d, 2.2) | 53.13 |
| 10 | 4.53 (d, 2.2) | 73.31 |
| 11 | — | 132.91 |
| 12 | — | 129.78 |
| 13 | — | 40.05 |
| 14 | — | 121.09 |
| 15$_1$ | 1.99 (dd, 3.6, 12.5) | 37.50 |
| 15$_2$ | 1.84 (ddd, 4.7, 12.5, 12.5) | |
| 16$_1$ | 2.64 (dd, 4.7, 14.3) | 40.85 |
| 16$_2$ | 2.42 (ddd, 3.6, 14.3) | |
| 3-OCH$_3$ | 3.86 (s) | 56.57 |
| 8-OCH$_3$ | 3.69 (s) | 57.06 | b) Physico-chemical data of (1)

Mass Spectroscopy (ESI-TOF$^+$): m/z 350.1 [M+H]$^+$

Mass calculated for C$_{18}$H$_{24}$NO$_6$: 350.1604

High Resolution MS (DCI$^+$): m/z 350.1604 [M+H]$^+$

UV ($\lambda_{max}$ nm ($\epsilon$), MeOH): 282 (3318), 242$_{sh}$ (9926), 207 (57483)

$[\alpha]^{20}_D$ −46° (c 0.5, MeOH)

Circular Dichroism ($\lambda$ext$_{nm}$, θ): (216, +66324), (227, −15949), (242, +16864)

(c=1.15×10$^{-3}$ M, MeOH)

2) Compound (2)

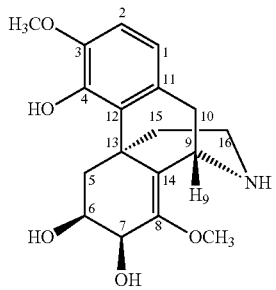

(2)

a) NMR data of (2)

$^1$H-NMR (300 MHz, CD$_3$OD): δ 6.85 (d, 1H, J=8.3 Hz), 6.62 (dd, 1H, J=1.2, 8.3 Hz), 4.96 (dd, 1H, J=1.7, 6.2 Hz), 4.39 (dd, 1H, J=1.1, 3.1 Hz), 3.87 (ddd, 1H, J=3.1, 3.9, 13.5 Hz), 3.84 (s, 3H), 3.78 (s, 3H), 3.31 (ddd, 3H, J=1.2, 6.2, 19.1 Hz), 3.14 (dd, 1H, J=4.6, 13.1 Hz), 3.10 (dd, 1H, J=1.7, 19.1 Hz), 3.03 (ddd, 1H, J=1.1, 3.9, 13.5 Hz), 2.84 (ddd, 1H, J=4.1, 13.1, 13.2 Hz), 2.24 (dd, 1H, J=13.5, 13.5 Hz), 2.19 (dd, 1H, J=4.1, 13.2 Hz), 2.06 (ddd, 1H, J=4.6, 13.2, 13.2 Hz)

$^{13}$C-NMR (300 MHz, CD$_3$OD): δ 33.53, 34.08, 36.0, 38.46, 40.67, 47.96, 56.22, 56.67, 65.38, 68.11, 111.30, 113.92, 119.48, 127.90, 128.56, 145.79, 148.09, 150.66

The NMR data of (2) were similar to those previously described in literature [1, 2].

b) Physico-chemical data of (2)

Mass Spectroscopy (ESI-TOF$^+$): m/z 334.1 [M+H]$^+$
Mass calculated for C$_{18}$H$_{24}$NO$_5$: 334.1654
High Resolution MS calculated for C$_{18}$H$_{23}$NO$_5$: 334.1655
UV (MeOH) λ$_{max}$nm (ε): 282 (2856), 242$_{sh}$ (6984), 207 (59602)

[α]$^{20}_D$ −143° (c 0.25, MeOH) cf. [3] [α]$^{20}_D$ −137.4° (c 0.12, MeOH)

Circular Dichroism (λext$_{nm}$, θ): (216, +63340), (227, −15231), (242, +16105)

(c=1.20×10$^{-3}$ M, MeOH)

cf. [1] CD (λext$_{nm}$, θ): (238, +62100) (c=9.67×10$^{-5}$ M, MeOH)

3) Stereochemistry of Compounds (1) and (2):

Specific rotation values of compound (2) and sinococuline were closely the same.

Compounds (1) and (2) showed the same Nuclear Overhauser Effect SpectroscopY (NOESY) correlations (cf. table 1) as sinococuline. Consequently compounds (1) and (2) have been assigned with the same relative configuration (6S*, 7S*, 9R*, 13S*) as sinococuline.

Moreover, compounds (1) and (2) exhibited similar CD spectra (positive maxima at 216 nm and 242 nm, negative maximum at 227 nm), in agreement with this of sinococuline described in literature, allowing us to conclude that the absolute configuration of compound (1) and compound (2) is (6S, 7S, 9R, 10R, 13S) and (6S, 7S, 9R, 13S) respectively.

TABLE 1

| | NOESY (2D-NMR, 400 MHz, MeOH) | |
|---|---|---|
| Proton n° | Compound (1) Correlated protons | Compound (2) Correlated protons |
| 1 | H10 | H2, H10$_1$, H10$_2$ |
| 2 | 3-OCH$_3$ | H1, 3-OCH$_3$ |

TABLE 1-continued

| | NOESY (2D-NMR, 400 MHz, MeOH) | |
|---|---|---|
| Proton n° | Compound (1) Correlated protons | Compound (2) Correlated protons |
| 3 | — | — |
| 4 | — | — |
| 5$_1$ | H15$_1$, H5$_2$, H6, H7 | H5$_2$, H6 |
| 5$_2$ | H5$_1$, H6 | H5$_1$, H6 |
| 6 | H15$_2$, H5$_2$, H5$_1$, H7 | H5$_1$, H5$_2$, H7, H15$_2$ |
| 7 | 8-OCH$_3$, H6 | 3-OCH$_3$, H5$_2$, 8-OCH$_3$ |
| 8 | — | — |
| 9 | 8-OCH$_3$, H10 | 8-OCH$_3$, H10$_1$, H10$_2$ |
| 10$_1$ | H16$_2$, H9, H1 | H1, H9, H10$_2$ |
| 10$_2$ | | H1, H9, H10$_1$ |
| 11 | — | — |
| 12 | — | — |
| 13 | — | — |
| 14 | — | — |
| 15$_1$ | H15$_2$, H16$_2$, H16$_1$, H5$_1$ | H5$_1$, H15$_2$, H16$_2$ |
| 15$_2$ | H15$_1$, H16$_1$, H6 | H6, H15$_1$, H16$_1$ |
| 16$_1$ | H15$_1$, H15$_2$, H16$_2$ | H15$_1$, H15$_2$, H16$_2$ |
| 16$_2$ | H15$_1$, H16$_1$, H10 | H15$_1$, H16$_1$ |
| 3-OCH$_3$ | H2 | H2 |
| 8-OCH$_3$ | H7, H9 | H7 |

Example 5

N-methyl-4,6,7,10-tetrahydroxy-8,14, didehydro-3,8-dimethoxy-morphinan (3)

C$_{19}$H$_{25}$NO$_6$

1) Preparation of Compound (3)

To a solution of (1) (10.9 mg, 0.031 mmol) in 1 mL MeOH was added 100 μl of a solution of formaldehyde (37% in water). After stirring for 1 hour at room temperature, 3 mg of NaBH$_4$ was added and the mixture was stirred for additional 3 hours.

After removal of the solvent under reduced pressure, the residue was acidified with 1N HCl, then basified with 20% aqueous NH$_4$OH and was further submitted to a silica gel column eluted with CH$_2$Cl$_2$-MeOH—NH$_4$OH (85-15-1), leading to compound (3) as a white solid (8 mg, 0.022 mmol), 71% yield.

2) Analytical Data of (3)

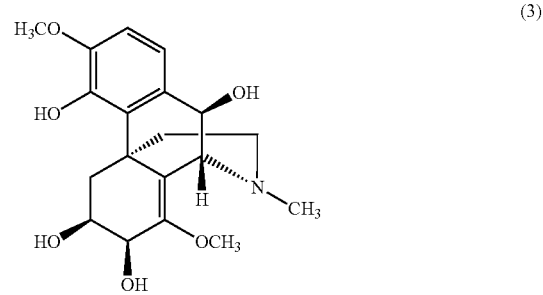

(3)

$^1$H-NMR (300 MHz, CD$_3$OD): δ 6.90 (d, 1H, J=8.4 Hz), 6.83 (d, 1H, J=8.4 Hz), 4.70 (d, 1H, J=2.2 Hz), 4.30 (dd, 1H, J=1.3, 3.4 Hz), 4.21 (d, 1H, J=2.2 Hz), 3.88 (m, 1H, J=3.4, 4.1, 13.8 Hz), 3.87 (s, 3H), 3.70 (s, 3H), 2.98 (ddd, 1H, J=1.3, 4.1, 13.8 Hz), 2.51 (dd, 1H, J=3.3, 12.4 Hz), 2.47 (s, 3H), 2.26 (m, 1H, J=2.9, 12.4, 12.9 Hz), 2.18 (dd, 1H, J=13.8, 13.8 Hz), 1.95 (m, 2H, J=2.9, 3.3, 12.9 Hz)

Mass Spectroscopy (ESI-TOF$^+$): m/z 364.1 [M+H]$^+$
Mass calculated for C$_{19}$H$_{26}$NO$_6$: 364.1760

High Resolution MS (DCI$^+$): m/z 364.1764 [M+H]$^+$
[α]$^{20}_D$ −41° (c 0.5, MeOH)

Example 6

N-propyl-4,6,7,10-tetrahydroxy-8,14,
didehydro-3,8-dimethoxy-morphinan (4)
$C_{21}H_{29}NO_6$ 1) Preparation of Compound (4)

To a solution of (1) (3.05 mg, 0.0087 mmol) in 300 µl MeOH, was added 1 µl, 0.014 mmol of propionaldehyde and 0.6 mg, 0.0095 mmol of sodium cyanoborohydride NaBH$_3$CN. The mixture was stirring for 4 hours at room temperature.

After removal of the solvent under reduced pressure, the residue was acidified with HCl 1N, then basified with 20% aqueous NH$_4$OH and was submitted to a preparative TLC eluted twice with CH$_2$Cl$_2$-MeOH—NH$_4$OH (90-10-1) to provide (4) as a white solid (2.3 mg, 0.0059 mmol), 68% yield.

2) Analytical Data of (4)

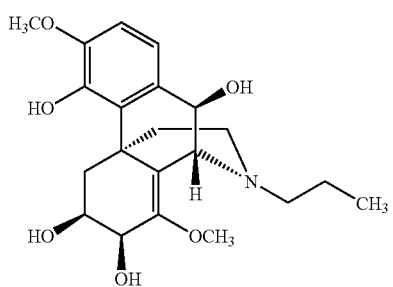
(4)

$^1$H-NMR (300 MHz, CD$_3$OD): δ 6.99 (d, 1H, J=8.4 Hz), 6.96 (d, 1H, J=8.4 Hz), 4.82 (d, 1H, J=1.9 Hz), 4.72 (s, 1H), 4.37 (d, 1H, J=3.3 Hz), 3.92 (m, 1H), 3.89 (s, 3H), 3.78 (s, 3H), 3.05 (m, 4H), 2.66 (m, 2H), 2.27 (dd, 1H, J=13.5, 13.5 Hz), 2.11 (dd, 1H, J=3.9, 12.3 Hz), 1.77 (m, 2H, J=2.2, 7.3, 7.3 Hz), 1.02 (t, 3H, J=7.3 Hz)

Mass Spectroscopy (ESI-TOF$^+$): m/z 392.2 [M+H]$^+$
Mass calculated for $C_{21}H_{30}NO_6$: 392.2073
High Resolution MS (DCI$^+$): m/z 392.2064 [M+H]$^+$
[α]$^{20}_D$ −18° (c 0.1 MeOH)

Example 7

N-4-methoxybenzyl-4,6,7,10-tetrahydroxy-8,14,
didehydro-3,8-dimethoxy-morphinan (5)
$C_{26}H_{31}NO_7$ 1) Preparation of Compound (5):

To a solution of (1) (5.7 mg, 0.016 mmol) in 500 µl MeOH, was added 200 µl, 1.6 mmol of anisaldehyde. After stirring for 1 hour at room temperature, 3 mg of NaBH$_4$ was added and the mixture was stirred for additional 3 hours at room temperature.

After removal of the solvent under reduced pressure, the residue was acidified with HCl 1 N, then basified with 20% aqueous NH$_4$OH and was submitted to a preparative TLC, eluted twice with CH$_2$Cl$_2$-MeOH—NH$_4$OH (90-10-1.5) to provide (5) as a white solid (3.0 mg, 0.0064 mmol), 40% yield.

2) Analytical Data of (5)

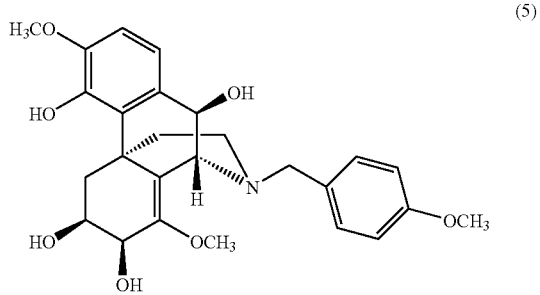
(5)

$^1$H-NMR (300 MHz, CD$_3$OD): δ 7.47 (d, 2H, J=8.6 Hz), 7.0 (d, 2H, J=8.6 Hz), 6.98 (d, 1H, J=8.4 Hz), 6.93 (d, 1H, J=8.4 Hz), 4.88 (s, 1H), 4.71 (s, 1H), 4.40 (d, 1H, J=2.8 Hz), 4.25 (s, 2H), 3.99 (m, 1H), 3.88 (s, 3H), 3.83 (s, 3H), 3.77 (s, 3H), 3.06 (m, 2H, J=3.6, 3.9, 12.5, 13.6 Hz), 2.75 (dd, 1H, J=2.1, 12.5 Hz), 2.28 (ddd, 1H, J=3.2, 13.6, 13.6 Hz), 2.20 (dd, 1H, J=3.9, 13.2 Hz), 2.07 (dd, 1H, J=2.1, 13.2 Hz)

MS (ESI-TOF$^+$): m/z 470.2 [M+H]$^+$
Mass calculated for $C_{26}H_{32}NO_7$: 470.2179
High Resolution MS (DCI$^+$): m/z 470.2170 [M+H]$^+$
[α]$^{20}_D$ −12° (c 0.1, MeOH)

Example 8

N-4-hydroxybenzyl-4,6,7,10-tetrahydroxy-8,14,
didehydro-3,8-dimethoxy-morphinan (6)
$C_{25}H_{29}NO_7$ 1) Preparation of Compound (6)

To a solution of (1) (4.85 mg, 0.014 mmol) in 500 µl of MeOH was added 4-hydroxy-benzaldehyde (1.7 mg, 1 eq). After stirring for 4 hours at room temperature, 0.9 mg, 1 eq of NaBH$_3$CN was added and the mixture was stirred for additional 3 hours at room temperature.

After removal of the solvent under reduced pressure, the residue was acidified with HCl 1N, then basified with 20% aqueous NH$_4$OH and was submitted to a preparative TLC, eluted twice with CH$_2$Cl$_2$-MeOH—NH$_4$OH (90-10-1) to provide (6) as a white solid (3.5 mg, 0.0077 mmol), 55% yield.

2) Analytical Data of (6)

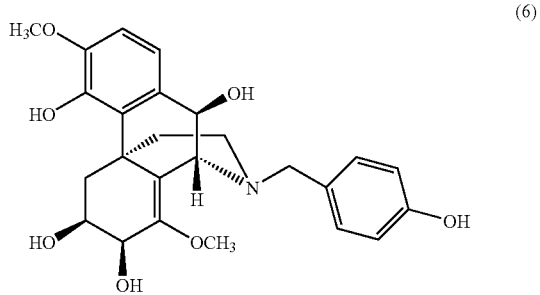
(6)

$^1$H-NMR (300 MHz, CD$_3$OD): δ 7.29 (d, 2H, J=8.6 Hz), 6.96 (d, 1H, J=8.4 Hz), 6.91 (d, 1H, J=8.4 Hz), 6.82 (d, 2H, J=8.6 Hz), 4.79 (s, 1H), 4.57 (d, 1H, J=1.6 Hz), 4.37 (d, 1H, J=3.3 Hz), 4.01 (d, 2H, J=8.1 Hz), 3.94 (ddd, 1H, J=3.7, 3.7, 12.9 Hz), 3.87 (s, 3H), 3.72 (s, 3H), 3.02 (dd, 1H, J=4.1, 13.5

Hz), 2.88 (d, 1H, J=12.6 Hz), 2.59 (ddd, 1H, J=3.7, 12.6, 12.6 Hz), 2.25 (dd, 1H, J=13.5, 13.5 Hz), 2.12 (ddd, 1H, J=4.5, 12.6, 12.6 Hz), 2.01 (d, 1H, J=12.6 Hz)

Mass Spectroscopy (ESI-TOF+): m/z 456.2 [M+H]+
Mass calculated for $C_{25}H_{30}NO_7$: 456.2022
High Resolution MS (DCI+): m/z 456.2018 [M+H]+
$[\alpha]^{20}_D$ −10° (c 0.03, MeOH)

Example 9

N-4-bromobenzyl-4,6,7,10-tetrahydroxy-8,14, didehydro-3,8-dimethoxy-morphinan (7)
$C_{25}H_{28}NO_6Br$ 1) Preparation of Compound (7)

To a solution of (1) (3.3 mg, 0.0095 mmol) in 300 μl MeOH was added 2 mg, 0.011 mmol of 4-bromo-benzaldehyde and 3 mg of NaBH₃CN. The mixture was stirred 20 hours at room temperature.

After removal of the solvent under reduced pressure, the residue was acidified with HCl 1N, then basified with 20% aqueous NH₄OH and was submitted to a preparative TLC eluted twice with CH₂Cl₂-MeOH—NH₄OH (95-5-0.5) to provide (7) as a white solid (3.0 mg, 0.0058 mmol), 61% yield.

2) Analytical Data of (7)

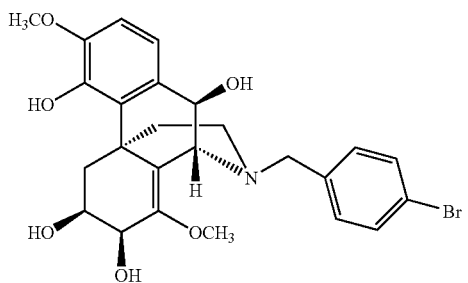

(7)

¹H-NMR (300 MHz, CD₃OD): δ 7.51 (d, 2H, J=8.4 Hz), 7.35 (d, 2H, J=8.4 Hz), 6.92 (d, 1H, J=8.4 Hz), 6.88 (d, 1H, J=8.4 Hz), 4.78 (d, 1H, J=3.4 Hz), 4.74 (s, 2H), 4.73 (d, 1H, J=2.2 Hz), 4.32 (d, 1H, J=1, 3.4 Hz), 3.93 (ddd, 1H, J=2.9, 3.4, 13.5 Hz), 3.88 (s, 3H), 3.68 (s, 3H), 3.0 (dd, 1H, J=2.9, 13.5 Hz), 2.66 (m, 1H, J=4.6, 12.1 Hz), 2.46 (ddd, 1H, J=3.9, 12.1, 12.1 Hz), 2.21 (dd, 1H, J=13.5, 13.5 Hz), 2.05 (ddd, 1H, J=4.6, 12.6, 12.6 Hz), 1.94 (ddd, 1H, J=1.9, 3.9, 12.6 Hz)

Mass Spectroscopy (ESI-TOF+): m/z 519.1 and 521.1 [M+H]+
Mass calculated for $C_{25}H_{29}NO_6Br$: 519.1035 and 521.1055
High Resolution MS (DCI+): m/z 519.1037 and 521.1058 [M+H]+
$[\alpha]^{20}_D$ −0.5° (c 0.5, MeOH)

Example 10

N-cyclopentyl-4,6,7,10-tetrahydroxy-8,14, didehydro-3,8-dimethoxy-morphinan (8)
$C_{23}H_{31}NO_6$ 1) Preparation of Compound (8)

To a solution of (1) (4.95 mg, 0.014 mmol) in 300 μl of MeOH was added 2 μl, 0.023 mmol of cyclopentanone and 3 mg of NaBH₃CN. The mixture was stirred for 6 hours at room temperature.

After removal of the solvent under reduced pressure, the residue was acidified with 1 N HCl, then basified with 20% aqueous NH₄OH and was submitted to a preparative TLC eluted twice with CH₂Cl₂-MeOH—NH₄OH (90-10-1) to provide (8) as a white solid (4.75 mg, 0.011 mmol), 81% yield.

2) Analytical Data of (8)

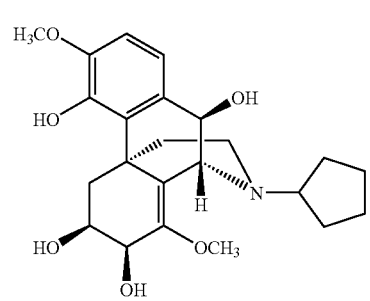

(8)

¹H-NMR (300 MHz, CD₃OD): δ 6.98 (d, 1H, J=8.4 Hz), 6.94 (d, 1H, J=8.4 Hz), 4.83 (s, 1H), 4.71 (s, 1H), 4.37 (d, 1H, J=2.7 Hz), 3.91 (m, 1H), 3.88 (s, 3H), 3.78 (s, 3H), 3.21 (d, 1H, J=12.6 Hz), 3.05 (dd, 1H, J=3.5, 14.3 Hz), 2.27 (m, 2H, J=12.6, 14.3 Hz), 2.16 (m, 1H), 1.86 (m, 4H), 1.65 (m, 6H)

Mass Spectroscopy (ESI-TOF+): m/z 418.2 [M+H]+
Mass calculated for $C_{23}H_{32}NO_6$: 418.2230
High Resolution MS (DCI+): m/z 418.2239 [M+H]+
$[\alpha]^{20}_D$ −30° (c 0.03, MeOH)

Evaluation of the Biological Activity of Compounds

Materials and Methods

In vitro Evaluation of the Antimalarial Activity of Plant Extracts and Pure Compounds (1)-(8)

A—Murine Model: Hepatic Stage of *Plasmodium yoelii yoelii* 265BY.

Primary cultures of mouse hepatocytes were isolated from livers of Swiss mice which were 6 to 8 weeks old by perfusion with collagenase (1 g/L) and purified through a 60% Percoll gradient.

The hepatocytes were cultured in sterile chambers (Lab-Tek) at the rate of 90,000 cells in 0.3 mL of complete culture medium as defined thereafter per well and incubated overnight at 37° C. under a 4% CO₂ atmosphere. The hepatocytes' complet culture medium was Williams' E culture medium supplemented with 10% of decomplemented foetal calf serum, 1% glutamine, 1% Na pyruvate, 1% of a mixture of insulin, transferrine and selenium, 1% of non-essential amino-acids and with an antibiotic mixture comprising 1% of a solution of penicillin and streptomycine, 1% augmentin and 2.5 pg/ml flucytosine.

The parasites infecting the hepatocytes; i.e. the sporozoites, were recovered by dissection of infected anopheles mosquitoes salivary glands.

After grinding them in a Potter grinder with culture medium, the suspension was filtered on a 40 μm mesh filter and centrifuged (15,000 rpm) at 4° C. for 2 mn. The pellet was reintroduced in the complete culture medium. The sporozoites were then counted in a "Cell Vu" counter (CML) and the concentration was adjusted at 100,000 sporozoites per 70 μL, concentration needed for infection.

One day after, the hepatocytes were infected by the above sporozoites from salivary glands of infected anopheles mosquitoes at the rate of 100,000 sporozoites per well in the presence or absence of the product to be tested. When the infection had appeared, the medium was supplemented with 10⁻⁷ M dexamethasone. The products were first solubilized in DMSO.

The infected hepatocytes were washed and fed with culture medium containing the test product, 3 hours and then 24 hours after the infection.

The cultures were stopped by treatment with a cold fixative methanol solution, 48 hours after the infection.

Parasites obtained in schizont stage were immunomarked firstly, with a serum isolated from BALB/c mice immunized with a recombinant fragment from the N-terminal of the recombinant protein I72 that reacted against HSP70 of *Plasmodium* [4] and secondly with an antibody—a mouse anti-immunoglobulin—conjugated to FITC. Evans Blue and DAPI, a nucleic acid marker, were added to the hepatocytes simultaneously. The schizonts were then counted with a fluorescent microscope.

Extracts and purified products exhibiting a significant inhibition effect on *P. yoelii yoelii* 265BY growth in murine hepatocytes were tested on human hepatocyte cultures infected with *P. falciparum* NF54.

B—Human Model: Hepatic Stage of *Plasmodium falciparum* NF54

Human hepatocytes were obtained by enzymatic perfusion of fragments of liver of human adults which were submitted to partial hepatectomy.

The hepatocytes were infected at 24 hours of their culture by sporozoites obtained from salivary glands of *P. falciparum* infecting anopheles mosquitoes *stephensi* (Lab. of Pr. W. Eling, Univ. Of Nijmegen, NL).

The culture medium containing the test product was changed 3 hours after infection, and then renewed at least, each 24 hours during the experiment.

The cultures were fixed 5 days after infection, with the same method as described for the murine hepatocytes [5].

The $CI_{50}$ value (concentration causing 50% of inhibition in the number of parasites compared to controls wells, non treated) is the mean value of 3 independent evaluations through StatView SI Graphics.

In vitro Evaluation of the Cytotoxicity of Plant Extracts and Pure Compounds (1)-(8)

The cytotoxicity assays were carried out in 96-well microliter plates, in triplicate, against human carcinoma KB cell line (ATCC CCL-17) (10⁴ cells/mL in DMEM medium) and human colon tumor HT29 cell line (ATCC HTB-38) (10⁵ cells/mL in RPMI 1640 medium), both supplemented with 10% foetal calf serum, L-glutamine (2 mM), penicillin G (100 UI/mL), streptomycin (100 μg/mM) and gentamycin (10 μg/mL).

Stock solutions of testing compounds were prepared in $H_2O$/DMSO (9/1).

After an incubation of 72 hours at 37° C. under a 5% $CO_2$ atmosphere, 0.02% of neutral red in PBS was added.

24 hours later, culture media were eliminated and cell membranes were lysed by addition of 1% of SDS in water.

Cell growth was estimated by colorimetric measurement of stained living cells, incorporating neutral red. Optical density was determined at 540 nm on a Titertek Multiskan photometer.

The $CI_{50}$ value was defined as the concentration of compound necessary to inhibit the cell growth to 50% of the control.

Results

Table 2 represents in vitro activities of natural compounds (1) and (2) and N-substituted derivatives of (1), compounds (3)-(8), on growth inhibition of *P. yoelii yoelii* 265 BY in murine hepatocytes and their cytotoxicity on human tumor cell lines.

In Table 2, R represents the group introduced on the nitrogen atom by chemical modification of (1) as defined in formula I.

The selectivity index (=ratio between $CI_{50}$ of cytotoxicity and $CI_{50}$ of anti-malarial activity) that was calculated, should the real effect of the compounds on *Plasmodium* parasites with respect to mammalian cells.

Primaquine and atovaquone were tested as references for their inhibiting activities on hepatic stage of *Plasmodium*, while 5-fluorouracile and vinblastine were tested as references for their cytotoxic activities on KB and HT29 cells.

TABLE 2

| Compound —R₁₀ | $CI_{50}$ activity *P. yoelii* 265BY in μg/mL, (μM) | $CI_{50}$ cytotoxicity KB in μg/mL, (μM) | $CI_{50}$ cytotoxicity HT29 in μg/mL, (μM) | Selectivity index $CI_{50}$ KB/$CI_{50}$ yoelii |
|---|---|---|---|---|
| (1) —H | 1.08 [0.15-0.32] 3.1 | 1.99 ± 1.3 5.7 | 22.0 ± 12.5 63.0 | 1.8 |
| (2) —H | 1.50 [0.25-0.45 4.5 | 1.30 ± 0.6 3.9 | 12.24 ± 8.59 36.8 | 0.9 |
| (3) —CH3 | 2.09 [0.87-0.67] 5.8 | 32.31 ± 7.1 89.0 | >80 >220 | 15.5 |
| (4) —CH2—CH2—CH3 | 4.93 [0.69-0.60] 12.6 | 40.37 ± 13.9 103.2 | >80 >204 | 8.2 |
| (5) 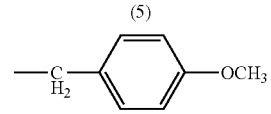 | 11.4 [0.75-0.64] 24.2 | 21.23 ± 6.2 45.3 | >80 >170 | 1.9 |

TABLE 2-continued

| Compound —R$_{10}$ | CI$_{50}$ activity P. yoelii 265BY in µg/mL, (µM) | CI$_{50}$ cytotoxicity KB in µg/mL, (µM) | CI$_{50}$ cytotoxicity HT29 in µg/mL, (µM) | Selectivity index CI$_{50}$ KB/CI$_{50}$ yoelii |
|---|---|---|---|---|
| (6) 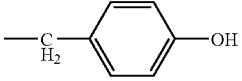 | 6.44 [0.92-0.80] 14.2 | 9.53 ± 3.3 20.9 | 48.96 ± 1.8 107.6 | 1.5 |
| (7) 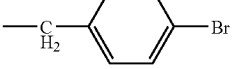 | 2.19 [0.92-0.71] 4.2 | 15.81 ± 6.4 30.5 | >80 >154 | 7.3 |
| (8) 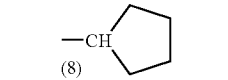 | 1.46 [1.01-0.89] 3.5 | 27.64 ± 9.0 66.28 | >80 >192 | 18.9 |
| primaquine | 0.16 [0.11-0.28] 0.6 | 2.0 ± 0.9 7.0 | 20.12 ± 2.1 70.51 | 11.7 |
| Atovaquone | 0.021 [0.003-.009] 0.057 | 18.60 ± 8.7 50.8 | 44.60 ± 10.3 122 | 891.2 |
| 5-fluorouracile | / | 0.047 ± 0.03 0.36 | 54.88 ± 2.4 422 | / |
| Vinblastine | / | 0.018 ± 0.006 0.022 | 0.0080 ± 0.004 0.0099 | / |

Table 3 represents in vitro activities of natural compounds (1) and (2), on *P. falciparum* NF54 in human hepatocytes.

TABLE 3

| | CI$_{50}$ activity P. falciparum NF54 in µg/mL, (µM) |
|---|---|
| (1) | 1.51 [1.01-0.34] 4.3 |
| (2) | 3.36 [1.35-0.92] 10.1 |

In vivo Evaluation of the Antimalarial Activity of Compound (1)

40 Swiss mice (six week old) have been subjected to the in vivo assay. They have been allotted in two groups:
- a group of 20 mice were fed with compound (1) diluted in sterile water at a dose of 100 mg/kg four times; 24 hours and 1 hour before infection, 24 hours and 40 hours after infection during the hepatic stage period.
- a control group of 20 mice were fed with sterile water at the same times.

The infection has been performed by retro-orbital injection of 4,000 sporozoites of *Plasmodium yoelii yoelii* 265BY in 100 µl phospate-buffered saline per mouse.

The parasitemia was monitored from the third day after the infection D3 when the parasites are liberated from the liver and enter into the blood circulation and each day until the 23rd day D23 after infection. The monitoring was performed by blood smears taken from the tail vein of the mice. The smears were stained with Giemsa and parasited red blood cells were counted with a microscope.

The parasitemia was calculated according to the following formula:

Parasited red blood cell number×100/total red blood cell number.

Results

The following table presents the obtained results.

| Number of parasited mice/20 total mice | Days post-infection | | | | | | |
|---|---|---|---|---|---|---|---|
| | D3 | D4 | D5 | D6 | D7 | D8 | D23 |
| Control Group | 20/20 | 20/20 | 20/20 | 20/20 | 20/20 | 20/20 | 15/15 |
| Treated group with compound (1) | 0/20 | 0/20 | 0/20 | 1/20 | 4/20 | 6/20 | 6/18 |

None of the treated mice were parasited at the fifth day after the infection whereas 100% of the control mice were parasited as soon as the third day.

In the treated group, the first mouse was parasited at the sixth day after infection with a delay of 3 days compared to the control group mice. At the end of the assay, on the 23$^{rd}$ day, only 6 of the 20 treated mice were parasited, whereas 100% of the control mice were parasited. The results are set forth in FIG. 1.

As a first conclusion the treatment with compound (1) at 100 mg/kg allows a 70% total protection against malaria infection in mice, but also it allows a minimum 3 days delay for the 30% of treated mice, which were not protected.

As a second conclusion, the treatment with compound (1) at 100 mg/kg allows a better survival of mice at D23 in the treated group (90%) compared to the control group (75%).

Furthermore, the mean percentage of parasitemia was lower for mice parasited in the treated group compared to mice parasited in the control group (FIG. 1).

As a third conclusion, the treatment with compound (1) at 100 mg/kg allows a significant decrease of the number of parasited red blood cells.

The in vivo results confirm the in vitro results concerning the efficiency of compound (1) on the protection against

*Plasmodium yoelii* 265BY and *Plasmodium falciparum* NF54. Compound (1) in oral administration, protects mice against infection by *P. yoelii* 265BY (70%), reduces parasitemia, delays apparition of the parasites and improves mice survival.

This prophylactic treatment differs from the usual treatments which mainly target the blood forms of the parasite.

REFERENCES

[1] Itokawa H., Tsuruoka S., Takeya K., Mori N., Sonobe T., Kosemura S., Hamanaka T. An Antitumor Morphinane Alkaloid, Sinococuline, from *Cocculus trilobus*. *Chem. Pharm. Bull.*, 1987, 35, 1660-1662.
[2] Deng J.-Z., Zhao S.-X., Miao Z.-C. A Morphinan Alkaloid from roots of *Stephania cepharantha*. *Phytochemistry*, 1992, 31(4), 1448-1450.
[3] Hitotsuyanagi Y., Nishimura K., Ikuta H., Takeya K., Itokawa H. Synthesis of Antitumor morphinane Alkaloids, Sinococuline and 6-epi-, 7-epi-, and 6-epi-7-epi-Sinococuline, from Sinomenine. *J. Org. Chem.*, 1995, 60, 4549-4558.
[4] Motard A., Marussig M., Renia L., Baccam D., Landau I., Mattei D., Targett G., Mazier D. Immunization with the malaria heat shock like protein hsp70-1 enhances transmission to the mosquito. *Int. Immunol.*, 1995, 7(1), 147-50.
[5] Mazier D., Beaudoin R. L., Mellouk S., Druilhe P., Texier B., Trosper J., Miltgen F., Landau I., Paul C., Brandicourt O., et al. Complete development of hepatic stages of *Plasmodium falciparum* in vitro. *Science*, 1985, 227(4685), 440-2.

The invention claimed is:

1. A method for protecting against malaria infection in a subject or treating a subject suffering from malaria comprising: administering to said subject an effective amount of a compound of formula (I):

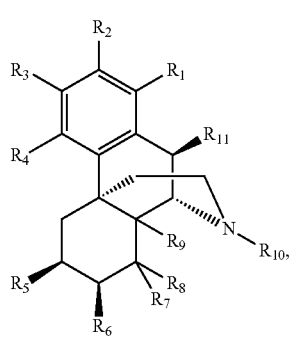

(I)

wherein
$R_1$ is H or $OC_iH_{2i+1}$ with i between 0 and 6;
$R_2$ is H or $OC_jH_{2j+1}$ with j between 0 and 6;
$R_3$ is H or $OC_kH_{2k+1}$ with k between 0 and 6;
$R_4$ is H or OH;
$R_5$ is OH or with $OC_mH_{2m+1}$ between 1 and 6 or an acetoxy group or an oxo group;
$R_6$ is OH or $OC_nH_{2n+1}$ with n between 1 and 6 or an acetoxy group or an oxo group;
$R_7$ is $OC_pH_{2p+1}$ with p between 0 and 6;
$R_8$ and $R_9$ may be similar or different and represent H or $OC_qH_{2q+1}$ with q between 0 and 6, or Hal where Hal is Cl, Br, F or I, or form together a covalent bond whereby the bond is a double bond or an ether bond (epoxy group);
$R_{10}$ is H or $C_rH_{2r+1}$ with r between 1 and 12 or an unsaturated alkyl group or a cycloalkyl group (tri- to hexa-) unsaturated or not, with or without heteroatoms; or an aromatic or a polycyclic aromatic group with or without heteroatoms; or $C_sH_{2s}$-A with s between 1 and 12 and whereby A is a saturated or (tri- to hexa-) unsaturated cycloalkyl group, with or without heteroatoms or an aromatic or a polycyclic aromatic group with or without heteroatoms or A is $C_6H_{5-t}$-(Hal)$_t$ with t between 1 to 5 or $C_6H_{5-u}$—(O—$C_vH_{2v+1}$)$_u$ with u between 1 to 5 and v between 0 and 6; or $R_{10}$ represents two substituents similar or different rendering the nitrogen atom quaternized, or an oxygen atom (nitrone group) and in which case the bond between the nitrogen atom and $C_9$ is a double bond; or $R_{10}$ represents $CH_2CH_2[OCH_2CH_2]_w$ $OCH_2CH_2$—B with w between 0 and 10 and where B is OH, O-D or NH-D where D is a $C_1$-$C_{12}$ alkyl group bearing an electrophilic function such as an isothiocyanate;
$R_{11}$ is H or OH or $OC_xH_{2x+1}$ with x between 1 and 6 or Hal where Hal is Cl, Br, F or I; or an acetoxy group or a sulfonate ester group or an oxo group; or $R_{10}$ and $R_{11}$ may represent an isoalkylidene group;
or a compound of formula (II):

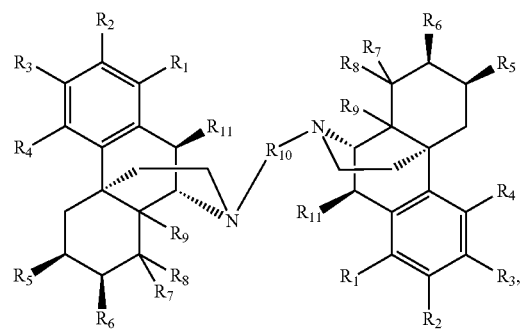

(II)

wherein
$R_1$, $R_2$, $R_3$, $R_5$, $R_6$, $R_7$, $R_8$ and $R_9$ are defined as above;
$R_4$ is H or OH or $OC_lH_{2l+1}$ with l between 2 and 6;
$R_{10}$ is $C_yH_{2y}$ with y between 1 and 12 or $CH_2CH_2[OCH_2CH_2]_zCH_2CH_2$ with z between 0 and 10; and
$R_{11}$ is H or OH or $OC_xH_{2x+1}$ with x between 1 and 6 or Hal where Hal is Cl, Br, F or I; or an acetoxy group or a sulfonate ester group or an oxo group;
all stereoisomers and optical isomers of said formula I or formula II or pharmaceutically acceptable salts thereof.

2. A method for treating a subject suffering from malaria comprising: administering to said subject an effective amount of a compound of formula (I)

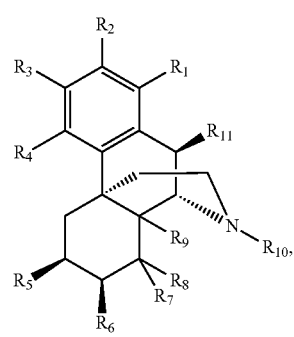

(I)

wherein
- $R_1$ is H or $OC_iH_{2i+1}$ with i between 0 and 6;
- $R_2$ is H or $OC_jH_{2j+1}$ with j between 0 and 6;
- $R_3$ is H or $OC_kH_{2k+1}$ with k between 0 and 6;
- $R_4$ is H or OH;
- $R_5$ is OH or $OC_mH_{2m+1}$ with m between 1 and 6 or an acetoxy group or an oxo group;
- $R_6$ is OH or $OC_nH_{2n+1}$ with n between 1 and 6 or an acetoxy group or an oxo group;
- $R_7$ is $OC_pH_{2p+1}$ with p between 0 and 6;
- $R_8$ and $R_9$ may be similar or different and represent H or $OC_qH_{2q+1}$ with q between 0 and 6, or Hal where Hal is Cl, Br, F or I, or form together a covalent bond whereby the bond is a double bond or an ether bond (epoxy group);
- $R_{10}$ is H or $C_rH_{2r+1}$ with r between 1 and 12 or an unsaturated alkyl group or a cycloalkyl group (tri- to hexa-) unsaturated or not, with or without heteroatoms; or an aromatic or a polycyclic aromatic group with or without heteroatoms; or $C_sH_{2s}$-A with s between 1 and 12 and whereby A is a saturated or (tri- to hexa-) unsaturated cycloalkyl group, with or without heteroatoms or an aromatic or a polycyclic aromatic group with or without heteroatoms or A is $C_6H_{5-t}$-(Hal)$_t$ with t between 1 to 5 or $C_6H_{5-u}$—(O—$C_vH_{2v+1}$)$_u$ with u between 1 to 5 and v between 0 and 6; or $R_{10}$ represents two substituents similar or different rendering the nitrogen atom quaternized, or an oxygen atom (nitrone group) and in which case the bond between the nitrogen atom and $C_9$ is a double bond; or $R_{10}$ represents $CH_2CH_2[OCH_2CH_2]_w$ $OCH_2CH_2$—B with w between 0 and 10 and where B is OH, O-D or NH-D where D is a $C_1$-$C_{12}$ alkyl group bearing an electrophilic function such as an isothiocyanate;
- $R_{11}$ is H or OH or $OC_xH_{2x+1}$ with x between 1 and 6 or Hal where Hal is Cl, Br, F or I; or an acetoxy group or a sulfonate ester group or an oxo group; or $R_{10}$ and $R_{11}$ may represent an isoalkylidene group;

or, of formula (II):

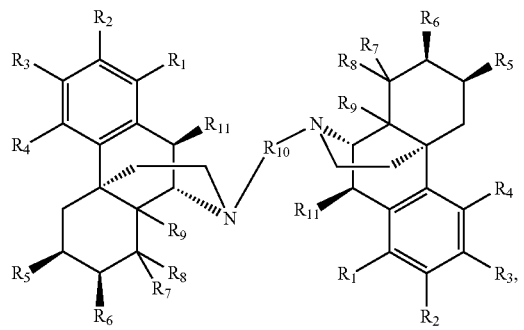

(II)

wherein
- $R_1$, $R_2$, $R_3$, $R_5$, $R_6$, $R_7$, $R_8$ and $R_9$ are defined as above;
- $R_4$ is H or OH or $OC_lH_{2l+1}$ with l between 2 and 6;
- $R_{10}$ is $C_yH_{2y}$ with y between 1 and 12 or $CH_2CH_2$ $[OCH_2CH_2]_zOCH_2CH_2$ with z between 0 and 10; and
- $R_{11}$ is H or OH or $OC_xH_{2x+1}$ with x between 1 and 6 or Hal where Hal is Cl, Br, F or I; or an acetoxy group or a sulfonate ester group or an oxo group;

all stereoisomers and optical isomers thereof of said formula I or formula II or pharmaceutically acceptable salts thereof.

3. Chemical compound of formula (I)

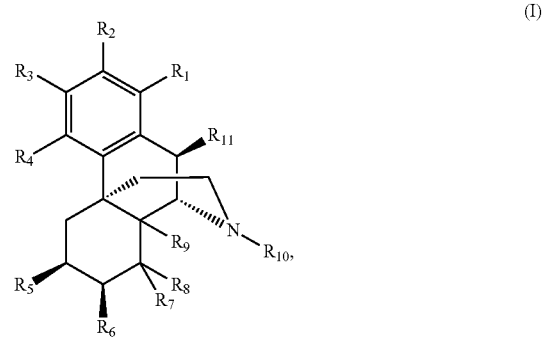

(I)

wherein
- $R_1$ is H or $OC_iH_{2i+1}$ with i between 0 and 6;
- $R_2$ is H or $OC_jH_{2j+1}$ with j between 0 and 6;
- $R_3$ is H or $OC_kH_{2k+1}$ with k between 0 and 6;
- $R_4$ is H or OH;
- $R_5$ is OH or $OC_mH_{2m+1}$ with m between 1 and 6 or an acetoxy group or an oxo group;
- $R_6$ is OH or $OC_nH_{2n+1}$ with n between 1 and 6 or an acetoxy group or an oxo group;
- $R_7$ is $OC_pH_{2p+1}$ with p between 0 and 6;
- $R_8$ and $R_9$ may be similar or different and represent H or $OC_{ql\ H2q+1}$ with q between 0 and 6, or Hal where Hal is Cl, Br, F or I, or form together a covalent bond whereby the bond is a double bond or an ether bond;
- $R_{10}$ is H or $C_rH_{2r+1}$ with r between 1 and 12 or an unsaturated alkyl group or a cycloalkyl group (tri- to hexa-) unsaturated or not, with or without heteroatoms; or an aromatic or a polycyclic aromatic group with or without heteroatoms; or $C_sH_{2s}$-A with s between 1 and 12 and whereby A is a saturated or (tri- to hexa-) unsaturated cycloalkyl group, with or without heteroatoms or an aromatic or a polycyclic aromatic group with or without heteroatoms or A is $C_6H_{5-t}$-(Hal)$_t$ with t between 1 to 5 or $C_6H_{5-u}$—(O—$C_vH_{2v+1}$)$_u$ with u between 1 to 5 and v between 0 and 6; or $R_{10}$ represents two substituents similar or different rendering the nitrogen atom quaternized, or an oxygen atom (nitrone group) and in which case the bond between the nitrogen atom and $C_9$ is a double bond; or $R_{10}$ represents $CH_2CH_2[OCH_2CH_2]_w$ $OCH_2CH_2$—B with w between 0 and 10 and where B is OH, O-D or NH-D where D is a $C_1$-$C_{12}$ alkyl group bearing an electrophilic function such as an isothiocyanate;
- $R_{11}$ is H or OH or $OC_xH_{2x+1}$ with x between 1 and 6 or Hal where Hal is Cl, Br, F or I; or an acetoxy group or a sulfonate ester group or an oxo group; or $R_{10}$ and $R_{11}$ may represent an isoalkylidene group;

or a compound of formula (II)

(II)

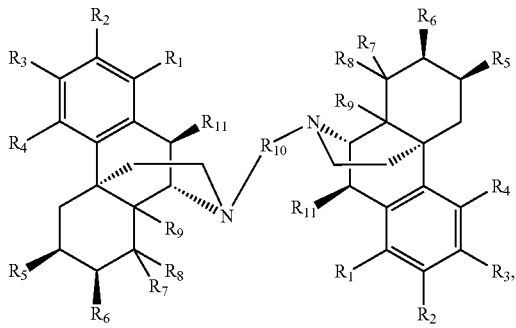

wherein
$R_1$, $R_2$, $R_3$, $R_5$, $R_6$, $R_7$, $R_8$ and $R_9$ are defined as above,
$R_4$ is H or OH or $OC_lH_{2l+1}$ with l between 2 and 6;
$R_{10}$ is $C_yH_{2y}$ with y between 1 and 12 or $CH_2CH_2[OCH_2CH_2]_zOCH_2CH_2$ with z between 0 and 10; and
$R_{11}$ is H or OH or $OC_xH_{2x+1}$ with x between 1 and 6 or Hal where Hal is Cl, Br, F or I; or an acetoxy group or a sulfonate ester group or an oxo group;
all stereoisomers and optical isomers of said formula (I) or formula (II),
and their pharmaceutically acceptable salts,
with the proviso that in formula (I), (1) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bond and $R_1$, $R_{10}$ and $R_{11}$ are H; (2) $R_1$ is not H when $R_2$ is H and $R_3$ and $R_7$ are $OCH_3$, $R_4$, $R_5$ and $R_6$ are OH and $R_8$ and $R_9$ represent a double bond and $R_{10}$ and $R_{11}$ are H; and (3) $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bond and $R_1$ is H.

4. A pharmaceutical composition comprising a compound according to claim 3, and a pharmaceutically acceptable vehicle.

5. A pharmaceutical composition comprising a compound of formula (I)

(I)

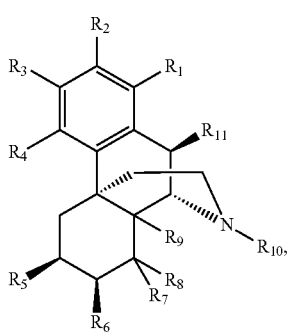

wherein
$R_1$ is H or $OC_iH_{2i+1}$ with i between 0 and 6;
$R_2$ is H or $OC_jH_{2j+1}$ with j between 0 and 6;
$R_3$ is H or $OC_kH_{2k+1}$ with k between 0 and 6;
$R_4$ is H or OH;
$R_5$ is OH or $OC_mH_{2m+1}$ with m between 1 and 6 or an acetoxy group or an oxo group;
$R_6$ is OH or $OC_nH_{2n+1}$ with n between 1 and 6 or an acetoxy group or an oxo group;
$R_7$ is $OC_pH_{2p+1}$ with p between 0 and 6;
$R_8$ and $R_9$ may be similar or different and represent H or $OC_qH_{2q+1}$ with q between 0 and 6, or Hal where Hal is Cl, Br, F or I, or form together a covalent bond whereby the bond is a double bond or an ether bond;
$R_{10}$ is H or $C_rH_{2r+1}$ with r between 1 and 12 or an unsaturated alkyl group or a cycloalkyl group (tri- to hexa-) unsaturated or not, with or without heteroatoms; or an aromatic or a polycyclic aromatic group with or without heteroatoms; or $C_sH_{2s}$-A with s between 1 and 12 and whereby A is a saturated or (tri- to hexa-) unsaturated cycloalkyl group, with or without heteroatoms or an aromatic or a polycyclic aromatic group with or without heteroatoms or A is $C_6H_{5-t}$-$(Hal)_t$ with t between 1 to 5 or $C_6H_{5-u}$—$(O-C_vH_{2v+1})_u$ with u between 1 to 5 and v between 0 and 6; or $R_{10}$ represents two substituents similar or different rendering the nitrogen atom quaternized, or an oxygen atom (nitrone group) and in which case the bond between the nitrogen atom and $C_9$ is a double bond; or $R_{10}$ represents $CH_2CH_2[OCH_2CH_2]_w OCH_2CH_2$—B with w between 0 and 10 and where B is OH, O-D or NH-D where D is a $C_1$-$C_{12}$ alkyl group bearing an electrophilic function such as an isothiocyanate;

$R_{11}$ is OH;

all stereoisomers and optical isomers of said formula (I), and their pharmaceutically acceptable salts, provided that $R_2$ is not H or alcoxy when $R_3$ is OH or alcoxy and $R_4$ is H or OH and $R_5$ and $R_6$ are OH or acyloxy and $R_7$ is $OCH_3$ and $R_8$ and $R_9$ represent a double bond and $R_1$ is H;

and a pharmaceutically acceptable vehicle.

6. The method according to claim 1, wherein the method is for treating a subject suffering from malaria.

7. The method according to claim 2, wherein the subject suffers from hepatic stage malaria.

* * * * *